(12) United States Patent
Kline

(10) Patent No.: US 7,842,314 B2
(45) Date of Patent: Nov. 30, 2010

(54) METHODS AND COMPOSITIONS FOR TREATING NEOPLASMS

(75) Inventor: Ellis L. Kline, Pendelton, SC (US)

(73) Assignee: Signal Coordinating Therapy, Inc., Pendleton, SC (US)

(*) Notice: Subject to any disclaimer, the term of this patent is extended or adjusted under 35 U.S.C. 154(b) by 241 days.

(21) Appl. No.: 11/258,548

(22) Filed: Oct. 25, 2005

(65) Prior Publication Data

US 2006/0034821 A1 Feb. 16, 2006

Related U.S. Application Data

(62) Division of application No. 09/827,302, filed on Apr. 5, 2001, now Pat. No. 6,977,169.

(60) Provisional application No. 60/195,538, filed on Apr. 7, 2000.

(51) Int. Cl.
*A01N 65/00* (2009.01)
(52) U.S. Cl. ...................................................... 424/725
(58) Field of Classification Search ........................ None
See application file for complete search history.

(56) References Cited

U.S. PATENT DOCUMENTS

| | | | | |
|---|---|---|---|---|
| 3,259,550 | A * | 7/1966 | Stacey et al. | 435/200 |
| 3,792,159 | A | 2/1974 | Green et al. | |
| 4,071,408 | A | 1/1978 | Flashner et al. | |
| 5,558,863 | A | 9/1996 | Kline et al. | |
| 5,645,997 | A * | 7/1997 | Kline et al. | 435/7.1 |
| 5,736,133 | A | 4/1998 | Kline et al. | |

FOREIGN PATENT DOCUMENTS

WO  WO 94/07516 A1  4/1994

OTHER PUBLICATIONS

Mayo Clinic, Leukemia-treatment, 2 pages, 2008.*
Gautam, S., et al., "Immuno-therapy of Methyl Cholanthrene Induced and Spontaneous Tumors in Mice by Use of Tumor Vaccine, Neuraminidase and BCG," *Indian J. Med. Res.*, vol. 64, No. 3, pp. 472-481 (1976).
Knop, J., et al., "Stimulatory Effect of Vibrio Cholerae Neuraminidase on the Antibody Response to Various Antigens," *Immunology*, vol. 34, pp. 181-187 (1978).
Mobley, J., "Phytomitogen and Neuraminidase in the Treatment of Ehrlich Carcinoma in Mice," *Research Communications in Chemical Pathology and Pharmacology*, vol. 9, No. 1, pp. 155-162 (1974).
Sedlacek, H., et al., "Immunotherapy of Neoplastic Diseases with Neuraminidase: Contradictions, New Aspects, and Revised Concepts," *Cancer Immunology and Immunotherapy*, vol. 5, pp. 153-163 (1978).
Sedlacek, H., et al., "Tumor Therapy of Neoplastic Diseases with Tumor Cells and Neuraminidase: Experimental Studies on Chessboard Vaccination in Transplantation Tumors," *Int. J. Immunopharmac.*, vol. 9, No. 7, pp. 841-850 (1987).
Sedlacek, H., et al., "Tumor Therapy of Neoplastic Diseases with Tumor Cells and Neuraminidase," *Cancer Immunology and Immunotherapy*, vol. 23, No. 1, pp. 192-199 (1986).
Simmons, R., et al., "Immunospecific Regression of Methylcholanthrene Fibrosarcoma With The Use of Neuraminidase. II. Intratumor Injections of Neuraminidase," *Surgery*, vol. 71, No. 4, pp. 556-564 (1972).
Simmons, R., et al., "Regression of Established Methylcholanthrene Tumors by Intratumor Injections of Vibrio Cholerae Neuraminidase," *J. of Surgical Oncology*, vol. 4, No. 4, pp. 298-305 (1972).
Author: Dermer, G., Title: Another Anniversary for the War on Cancer, Publ: *Bio/Technology*, vol./Iss: 12, pp. 320, Date: Mar. 1, 1994.
Author: Gorman, C., Title: Cancer: How to Tell the Hype from the Hope, Publ: *Time Magazine*, vol./Iss: pp. 38-46, Date: May 18, 1998.
Author: Gura, T., Title: Cancer Models: Systems for Identifying New Drugs are Often Faulty, Publ: *Science*, vol./Iss: 278, pp. 1041-1042, Date: Nov. 7, 1997.
Author: Jain, R., Title: Vascular and Interstitial Barriers to Delivery of Therapeutic Agents in Tumors, Publ: *Cancer and Metastasis Reviews*, vol./Iss: 9, pp. 253-266, Date: Jan. 1, 1990.
Author: Jain, R., Title: Delivery of Molecular Medicine to Solid Tumors, Publ: *Science*, vol./Iss: 271, pp. 1079-1080, Date: Feb. 23, 1996.
Author: Maiskii, I. et al., Title: Immunotherapeutic use of Neuraminidase in Chemically Induced Carcinogenesis, Publ: *Translated from Byulleten Eksperimental noi Biologii i Meditsiny*, vol./Iss: 84(12), pp. 1756-1759, Date: Dec. 1, 1977.
Author: Watkins, E. et al., Title: Neuraminidase-Mediated Augmentation of In Vitro Immune Response of Patients with Solid Tumors, Publ: *International Journal of Cancer*, vol./Iss: 14, pp. 799-807, Date: Jul. 1, 1974.

* cited by examiner

*Primary Examiner*—Michael V Meller
(74) *Attorney, Agent, or Firm*—Johnson & Associates

(57) ABSTRACT

The present invention comprises the periodic administration of a solution of neuraminidase to a patient with a neoplasm until the neoplasm has receded. The administration of the solution of neuraminidase can be administered by subcutaneous injection, intramuscular injection, intravenous injection, nasal administration, sublingual administration or transdermal administration. The present invention is effective in treating a wide variety of neoplasms.

10 Claims, No Drawings

METHODS AND COMPOSITIONS FOR TREATING NEOPLASMS

CROSS-REFERENCE TO RELATED APPLICATION

This application is a divisional of U.S. patent application Ser. No. 09/827,302 filed Apr. 5, 2001, now U.S. Pat. No. 6,977,169 which claims the benefit of to U.S. Provisional Application 60/195,538 filed Apr. 7, 2000.

FIELD OF THE INVENTION

The present invention is related to a method and composition for the treatment of neoplasms, including, but not limited to, malignant neoplasms. More particularly, the present invention is a method and composition comprising a solution or solid with a very low concentration of neuraminidase that is administered to a human or animal with a neoplasm.

BACKGROUND OF THE INVENTION

Cancer is a disease that ravages both human and animals. The term "cancer" means tumors or neoplasms, including malignant neoplasms, characterized by uncontrolled growth. Unlike normal cells, cancer cells are atypical in structure and do not have specialized functions. They compete with normal cells for nutrients, eventually killing normal tissue. Cancerous, or malignant, tissue can remain localized, invading only neighboring tissue, or can spread to other tissues or organs via the lymphatic system or blood (i.e., metastasize); virtually all tissues and organs are susceptible. It is a disease that is highly unpredictable and has a very high mortality rate. The current treatments for cancer include chemotherapy, surgery and radiation treatments. These radical treatment procedures are highly detrimental to the patient. For example, the typical chemotherapeutic agent is cytotoxic and has a very narrow therapeutic range. Therefore, the chemotherapeutic agent must be carefully administered at a dose that will kill cancer cells but not kill normal cells. These chemotherapeutic agents often leave the patient sick and weakened and are only minimally effective in treating the cancer.

What is needed is a composition and method for treating cancer that is not harmful to the patent but at the same time is effective in killing the cancer cells. Ideally, the composition and method can be used in combination with other agents.

SUMMARY OF THE INVENTION

The present invention provides a method and composition for treating a wide variety of neoplasms including, but not limited to, solid tumors, blood born tumors such as leukemias, tumor metastasis, benign tumors, for example hemangiomas, acoustic neuromas, neurofibromas, trachomas, and pyogenic granulomas. The present invention comprises administration to the human or animal with cancer of an effective amount of neuraminidase or a fraction or derivative thereof. The effective amount of neuraminidase, according to the present invention, is extremely low and does not cause side effects such as an immune response to the neuraminidase protein.

One embodiment of the present invention is a dilute solution of neuraminidase that can be systemically administered by a variety of routes including, but not limited to, intramuscularly, intradermally, intranasally, intravenously, sublingually, and subcutaneously. The present invention can also be administered locally to the site of the tumor. The preferable route of administration is multiple per day administrations sublingually.

Accordingly, it is an object of the present invention to provide a method for treating neoplasms including metastatic cancer.

It is yet another object of the present invention to provide a method and composition for the treatment of prostate cancer.

It is yet another object of the present invention to provide a method and composition for the treatment of breast cancer.

It is yet another object of the present invention to provide a method and composition for the treatment of colon cancer.

It is yet another object of the present invention to provide a method and composition for the treatment of ovarian cancer.

It is yet another object of the present invention to provide a method and composition for the treatment of leukemia.

It is yet another object of the present to provide a method and composition for the treatment of hemangioma.

It is yet another object of the present invention to provide a method and composition for the treatment of brain tumors.

It is yet another object of the present invention to provide a method and composition for the treatment of pancreatic tumors.

It is yet another object of the present invention to provide a method and composition for the treatment of liver tumors.

These and other objects, features, and advantages will become apparent after a review of the following detailed description of the disclosed embodiments and the appended claims.

DETAILED DESCRIPTION

As used herein, the term "neuraminidase" means any protein that has neuraminidase activity or has an amino acid sequence that is substantially similar to a protein which has neuraminidase activity. The term "neuraminidase" also includes fragments of neuraminidase that are effective in treating neoplasms The neuraminidase that can be used to practice the present invention can also be an inactivated enzyme wherein the neuraminidase has partial activity or no activity when compared to the activity of the native enzyme. It is believed that heating the neuraminidase in boiling water will destroy the antitumor activity.

The present invention provides a method and composition for treating neoplasms including, but not limited to, solid tumors, blood born tumors such as leukemias, tumor metastasis, benign tumors, for example hemangiomas, acoustic neuromas, neurofibromas, trachomas, and pyogenic granulomas. Examples of solid metastatic tumors or neoplasms include, but are not limited to, prostate cancer, pancreatic cancer, melanoma, breast cancer, esophageal cancer, lung cancer, colon cancer, testicular cancer, or brain cancer. It is to be understood that the present invention is effective against a wide variety of neoplasms.

The present invention comprises the administration of a neuraminidase to a patient with a cancer. The neuraminidase (Acyl-neuraminyl hydrolase: EC3.2.1.18) that can be used in practicing the present invention can be from any source including, but not limited to, *Arthrobacter ureafaciens, vibrio cholerae, Clostridium perfringens*.

Typically, a pharmaceutical dosage unit of the present invention for the delivery of neuraminidase in a low concentration comprises a liquid or solid pharmaceutically acceptable carrier and an effective amount of neuraminidase. The aforesaid effective amount is preferably from between approximately $10^{-2}$ to about $10^{-8}$ mg, and still more preferably about $10^{-4}$ mg neuraminidase in the dosage unit in association with pharmaceutically acceptable excipients. The preferred carrier is 0.1% to 0.4% phenol in 0.9% sodium chloride (USP).

The present invention comprises the administration of less than approximately $10^{-2}$ mg per dosage unit to a human or animal that has a tumor. A preferred dose of neuraminidase or active derivative thereof is between approximately $10^{-2}$ mg to $10^{-8}$ mg. A more preferred dose of neuraminidase is between approximately $10^{-3}$ mg and $10^{-7}$ mg. The most preferred dose of neuraminidase is approximately $10^{-4}$ mg. Preferably the total periodic daily dosage does not exceed about $10^{-2}$ mg per subject, and still more preferably does not exceed from about $10^{-3}$ mg to $10^{-4}$ mg.

In a second aspect of the invention there is provided a pharmaceutical composition comprising a vehicle for a single administration of neuraminidase or fraction or derivative thereof which comprises an amount of up to about $10^{-2}$ mg neuraminidase or fraction or derivative thereof and pharmaceutically inert ingredients. In a preferred aspect the pharmaceutical composition has an amount of between approximately $10^{-2}$ mg to about $10^{-8}$ mg neuraminidase or fraction or derivative thereof.

In practice, the present invention comprises the administration of an amount not to exceed approximately $10^{-2}$ mg, although, in certain cases, the total amount of neuraminidase administered in any one day may exceed the preferred limit. The neuraminidase can be administered as a liquid or it can be administered as a solid wherein the neuraminidase is embedded or admixed in a biodegradable or bioerodible matrix. The matrix can be a time release matrix. These matrices are well known to those of ordinary skill in the art and are not critical to the present invention. The neuraminidase can be administered by injection or by sub-lingual route. In one embodiment, the vehicle is an aqueous solution that is contained within an inert container. In another variation, the composition is in the form of a suppository. The liquid form of the composition can be injected subcutaneously, intramuscularly or intravenously. In addition, the composition can be administered through the mucosal membranes such as nasal membranes.

The neuraminidase can be administered through standard methods, including intravenous, intramuscular, and subcutaneous routes. The neuraminidase can also be administered by sublingual and intranasal routes. Because the effective amount of neuraminidase in a dose is so low, the composition according to the present invention can also be administered transdermally, anally or orally. The dosage units can be either liquid or solid. Typically, the dosage unit may be administered up to about 1 to 8 times per day or intermittently depending on the individual case.

The neuraminidase can be administered directly to the tumor site, but is preferably administered systemically. Preferred systemic administration for the present invention is via sublingual administration or nasal administration by administering a single drop (50 µl) of a neuraminidase solution (approximately $10^{-4}$ mg/dose). For the typical patient, the first day of treatment is an five dose regime in the first hour with four more doses spaced evenly during the day. The patient is treated four times per day after the first day until the malignancy and primary tumors are not detectable by extensive clinical examination. It is recommended that the patient remain on a maintenance regime of two to seven, preferably 4, administrations per day for several months to a year after the neoplasm is no longer detectable. The patient should be periodically examined for recurrence of the cancer. It is to be understood that the dosage per day regimes may be varied depending upon the patient response.

The preferred dosage for a typical cancer patient is as follows:

The first day, five doses are given in the first hour. The doses are given at time 0, 15, 30, 45 and 60 minutes in the morning, followed by three more applications evenly spaced throughout the day. Preferably, the doses are administered 15 minutes before eating or drinking. Continue daily dosing until manifestations of malignancy are no longer present. Maintain the 4 times a day dosing for 1 year longer to destroy any latent cancer cells.

Patient should be monitored for malignancies every 3 months by conventional monitoring methods well know to those of ordinary skill in the art while undergoing treatment. If dosing is discontinued, similar monitoring should continue every 3 months for one year. If there is any indication cancer returns, patient should immediately resume dosing regimen.

It is to be understood that the present invention may be used in combination with conventional therapies, including, but not limited to chemotherapy, surgery and radiation therapy. The present invention may be used in combination with these therapies or may be used before or after these therapies.

The invention is further illustrated by the following examples, which are not to be construed in any way as imposing limitations upon the scope thereof. On the contrary, it is to be clearly understood that resort may be had to various other embodiments, modifications and equivalents thereof which, after reading the description herein, may suggest themselves to those skilled in the art without departing from the spirit of the present invention and/or the scope of the appended claims. Patent summaries are from patients treated in Australian clinical trials.

EXAMPLE 1

Preparation of Neuraminidase 1 mg of neuraminidase (Sigma Chemical Co., St Louis, Mo.) is mixed with 1 ml of 0.9% saline (Allergy Laboratory, Inc., Oklahoma City, Okla.) saline. This solution is filter sterilized. 0.2 ml of this neuraminidase solution is mixed with 75 ml of 0.9% saline. This solution is allowed to stand at room temperature for three hours. Optionally, the solution is stirred every 15 minutes. After the three hour incubation at room temperature, 25 ml of 0.4% phenol saline is added to the 75 mls of neuraminidase saline solution. This gives a final phenol concentration of 0.1% in 0.9% saline solution and a final concentration of neuraminidase of $2\times10^{-3}$ mg/ml. This solution is kept at 4° C.

EXAMPLE 2

Alternative Method of Preparation of Neuraminidase 1 mg of neuraminidase (Sigma Chemical Co., St Louis, Mo.) is mixed with 1 ml of 0.4% phenol (Allergy Laboratory, Inc., Oklahoma City, Okla.) saline. This solution is filter sterilized. 0.2 ml of this neuraminidase solution is mixed with 24.8 ml of the 0.4% phenol saline. This solution is allowed to stand at room temperature for three hours. Optionally, the solution is stirred every 15 minutes. After the three hour incubation at room temperature, 75 ml of saline is added to the 25 mls of neuraminidase/phenol saline solution. This gives a final phenol concentration of 0.1% in 0.9% saline solution and a final concentration of neuraminidase of $2\times10^{-3}$ mg/ml. This solution is kept at 4° C.

EXAMPLE 3

Administration of Neuraminidase Solution

A preferred route of administration of the present invention is sublingual administration. A dropper that delivers 50 µl per drop is used to deliver one drop per administration sublingual. As stated above, the first day of treatment comprises the administration of one 50 µl drop every 15 minutes for one hour (5 drops total). After the first day, the patient is given one 50 µl drop four times a day until tumors have regressed. A recommended schedule is one drop before breakfast, one drop before lunch, one drop before supper, and one drop before bedtime. It is recommended that this schedule be maintained for several months to a year after all clinical signs of the cancer are gone. The patient should be closely monitored clinically and treatment resumed if the cancer returns.

EXAMPLE 4

A 51 year old male patient with testicular cancer that had metastasized to the prostate, intestine, liver and pancreas (stage 4) was treated as described above. After 6 months of neuraminidase sublingual treatment, there was no malignancy detectable. The patient maintained two sublingual applications daily as a prophylactic.

EXAMPLE 5

Lung cancer metastasized to liver and other tissues, with heavily involved lymph nodes, in a 34 year old female. Treatment with the neuraminidase sublingual treatment began Jul. 12, 1999. Steady improvement occurred over six months. By last physical examination in January 2000, there was no detection of any malignancy in any tissue.

EXAMPLE 6

The patient presented with non-operable brain tumor with extreme pain in head and compromised vision. After one and one half months of neuraminidase sublingual treatment, no pain nor vision impairment was reported. The patient continues on 4 applications of the neuraminidase solution of example 1 per day.

EXAMPLE 7

A second case of a patient with non-operable brain tumor was treated. After five months of treatment, all abnormal symptoms disappeared and clinical analysis shows no detectable signs of disorder. The patient continues on 4 applications of the neuraminidase solution of example 1 per day.

EXAMPLE 8

A 75 year old female presented with a B cell CD10 lymphoma. Diagnosis was based on clinical evaluation as well as tissue biopsy. Within one and one half months on the neuraminidase sublingual treatment, examination by an oncologist detected no abnormal CD10 transformed cells.

It should be understood, of course, that the foregoing relates only to a preferred embodiment of the present invention and that numerous modifications or alterations may be made therein without departing from the spirit and scope of the invention as set forth in the appended claims.

The invention claimed is:

1. A method for treating a human with leukemia, comprising administering to the human with leukemia a therapeutically effective amount of neuraminidase between approximately $10^{-2}$ and $10^{-8}$ mg per dose.

2. The method of claim 1, wherein the neuraminidase is dissolved in a phenol-saline solution.

3. The method of claim 1, wherein the neuraminidase is administered by subcutaneous injection, intramuscular injection, intravenous injection, nasal administration, sublingual administration or transdermal administration.

4. The method of claim 3, wherein the neuraminidase is administered sublingually.

5. The method of claim 1 wherein the neuraminidase is administered between approximately $10^{-3}$ and $10^{-7}$ mg per dose.

6. The method of claim 1 wherein the neuraminidase is administered at approximately $10^{-4}$ mg per dose.

7. The method of claim 1 wherein the neuraminidase is administered up to about 8 times per day.

8. The methods of claim 1 wherein the neuraminidase is administered between 2-7 times per day.

9. The method of claim 1 wherein the neuraminidase is administered for 4 times per day.

10. The method of claim 1 wherein on the first day of treatment, the neuraminidase is administered 5 times in the first hour followed by 3-4 more times evenly throughout the first day and then 2-7 times per day afterwards until the neoplasm is no longer detectable.

* * * * *